US005770155A

United States Patent [19]

Dunphy et al.

[11] Patent Number: 5,770,155

[45] Date of Patent: Jun. 23, 1998

[54] COMPOSITE STRUCTURE RESIN CURE MONITORING APPARATUS USING AN OPTICAL FIBER GRATING SENSOR

[75] Inventors: James R. Dunphy, South Glastonbury; Robert M. Rukus, South Windsor, both of Conn.; Jong-Min Ha, Seoul, Rep. of Korea

[73] Assignee: United Technologies Corporation, Hartford, Conn.

[21] Appl. No.: 560,268

[22] Filed: Nov. 21, 1995

[51] Int. Cl.$^{6}$ .................................................... G01N 21/17

[52] U.S. Cl. ................................ 422/82.05; 250/227.14; 250/227.18; 356/32

[58] Field of Search ............................ 422/82.05, 82.09; 250/227.18, 227.14; 356/32, 35.5; 264/40.1, 40.2; 73/800

[56] References Cited

U.S. PATENT DOCUMENTS

| | | | |
|---|---|---|---|
| 4,761,073 | 8/1988 | Meltz et al. | 356/32 |
| 4,798,954 | 1/1989 | Stevenson | 250/341 |
| 4,806,012 | 2/1989 | Meltz et al. | 356/32 |
| 4,827,121 | 5/1989 | Vidrine, Jr. et al. | 250/227 |
| 4,970,385 | 11/1990 | Tatsuno et al. | 250/225 |
| 4,996,419 | 2/1991 | Morey | 250/227.18 |
| 5,142,151 | 8/1992 | Varnell et al. | 250/339 |
| 5,158,720 | 10/1992 | Levy | 264/21 |
| 5,164,587 | 11/1992 | Caimi et al. | 250/227.17 |
| 5,265,475 | 11/1993 | Messinger et al. | 73/800 |
| 5,384,079 | 1/1995 | Bur et al. | 264/21 |
| 5,399,854 | 3/1995 | Dunphy et al. | 250/227.17 |
| 5,401,956 | 3/1995 | Dunphy et al. | 250/227.18 |
| 5,426,297 | 6/1995 | Dunphy et al. | 250/227.23 |
| 5,519,211 | 5/1996 | Bur et al. | 250/227.19 |

FOREIGN PATENT DOCUMENTS

| | | |
|---|---|---|
| 0 329 277 A2 | 8/1989 | European Pat. Off. . |
| 2 168 806 | 6/1986 | United Kingdom . |

OTHER PUBLICATIONS

Afromowitz, Martin A., "Fiber Optic Polymer Cure Sensor." Journal of Lightwave Technology, vol. 6, No. 10, Oct. 1988, pp. 1591–1594.

Claus, R. O. et al., "Embedded Optical Fiber Sensors for Materials Evaluation." Journal of Nondestructive Evaluation, vol. 8, No. 2, (Jun. 8, 1989), pp. 135–145.

Dunphy J. R. et al., "Multi–function, distributed optical fiber sensor for composite cure and response monitoring." *SPIE* vol. 1370 Fiber Optic Smart Structures and Skins III (1990), pp. 116–118.

Levy, R. L. "A New Fiber–Optic Sensor for Monitoring the Composite–Curing Process." Polymeric Materials Science and Engineering, vol. 54, (1984), pp. 321–324.

*Primary Examiner*—Jeffrey Snay
*Attorney, Agent, or Firm*—Gerald L. DePardo

[57] ABSTRACT

Resin curing of a composite laminated structure is monitored using an optical fiber 20 having a grating sensor 28 embedded therein. The fiber 20 is surrounded by upper and lower buffer regions 12,14 having a predetermined minimum number of layers 30 (or thickness) with uni-directional reinforcing filaments 32 and resin 34 therebetween. When the filaments 32 are oriented perpendicular to the longitudinal axis of the fiber 20, the buffer regions 12,14 allow the sensor 28 to exhibit maximum sensitivity to detection of the minimum resin viscosity and the gelation point (i.e., the onset of a rapid crosslinking rate) of the resin 34. The buffer regions 12,14 also have a minimum thickness which serve to isolate the sensor 28 from interfering stresses from arbitrarily angled filaments 32 in layers 30 of outer regions 10,16 which surround the buffer regions 12,14.

10 Claims, 5 Drawing Sheets

(λB) WAVELENGTH (μm)
1.300
1.298
1.296
1.294
1.292
1.290
TEMPERATURE
(°F)
400
350
300
250
200
150
100
50
0
TIME (SEC)
−1000
0
1000
2000
3000
4000
5000
6000
7000
100
200

(ΔλB) WAVELENGTH CHANGE (nm)
7.00000
5.00000
3.00000
1.00000
−1.00000
−3.00000
−5.00000
−7.00000
−1000
0
1000
2000
3000
4000
5000
6000
7000
8000
TIME
(SEC)
256
254
260
258
252
250

COMPOSITE STRUCTURE RESIN CURE MONITORING APPARATUS USING AN OPTICAL FIBER GRATING SENSOR

TECHNICAL FIELD

This invention relates to the monitoring of curing processes and more particularly to using optical fiber gratings to perform such monitoring.

BACKGROUND ART

It is known in the field of composite structures that composite laminated structures may be formed by common techniques including compression molding and resin transfer molding. For compression molding, layers made up of graphite filaments impregnated with an epoxy resin, are stacked to a predetermined thickness having a predetermined filament orientation for each of the layers. The resultant stacked preformed structure is called a "lay-up". The lay-up is placed into a hot press having pre-shaped molding tools set therein and the layers are pressed together and consolidated during a predetermined temperature and pressure time-profile. The profile typically comprises increasing the temperature until the resin begins to cure (or harden) while applying pressure to the lay-up. After the part reaches the full curing temperature and time, it is then cooled.

For one type of known resin transfer molding, the filaments are weaved together to form a "preform" structure having the desired filament lay-up orientation, and the preform is placed into a mold. Then, hot resin is injected into the mold and flows between the filaments to provide uniform resin infiltration throughout the structure. Next, the mold is heated, using an appropriate temperature and pressure profile to cure the resin, and then it is cooled.

One problem encountered in the art of manufacturing such composite structures is that the structure may have a varied thickness but the entire structure is exposed to a common temperature profile curing process. For complex geometry parts, the thinner regions may cure (harden) before the thicker regions. In such a case, non-uniform internal residual stress may build up, potentially compromising structural integrity of the part. Also, in the thicker regions, the outer layers may cure before the middle layers cure. In that case, if the middle layers out-gas (i.e., emit gasses during curing), the gas bubbles tend to permeate through the uncured layers and become trapped underneath the cured outer layers. Such trapped gas bubbles may create weaknesses in the lamination at the region where the bubbles collect, thereby weakening the structure and potentially causing premature de-lamination. These problems occur when the temperature profile is not designed such that both the thin region and the thick region uniformly cure.

However, if the through-the-thickness temperature distribution and resin viscosity within the composite structure could be monitored during the curing process, then the temperature profile may be varied accordingly so as to allow more uniform curing of both the thin and the thick portions of the composite structure, thereby enabling a more uniform curing across the entire structure. Thus, to optimize composite material curing processes for complex parts, sensors are needed to measure material changes during the consolidation process.

Two prior art techniques which are commonly used to determine curing process information are ultrasonic measurements and rheology measurements. An ultrasonic measurement device, as is known, comprises an ultrasonic transducer mounted on one side of the structure, which generates sound waves through the thickness of the structure, and an ultrasonic receiver on the other side of the structure, which receives such sound waves. The speed of the sound waves through the structure is directly related to the viscosity of the resin within the structure which propagates the wave. When the sound velocity increases significantly, rapid crosslinking (or hardening or gelation) has occurred. However, such a technique measures only the average viscosity in the volume spanned by the sound transmitter and receiver and, thus, does not provide a distributed measurement through the thickness of the structure.

Another technique known in the art is rheologic measurement. In that case, a portion of the material to be cured is analyzed by exerting twisting forces to determine viscosity characteristics as a function of temperature. However, such a technique is performed off-line, not during the curing process of the structure and, thus, is not a real time measurement procedure. Also, the time lapse between the off-line characterization and the actual curing of the material may result in aging differences between the characterized material and the material being cured.

DISCLOSURE INVENTION

Objects of the invention include provision of composite structure resin cure monitoring to optimize curing time, temperature, pressure, and chemistry.

According to the present invention a composite structure resin cure monitoring apparatus comprises an optical fiber having a grating sensor embedded therein; and buffer means disposed adjacent to the sensor for allowing the sensor to detect a minimum resin viscosity and a gelation point of the resin and for isolating the sensor from interfering stresses from other portions of the composite structure.

According further to the present invention, the buffer means comprises a predetermined number of layers each of the layers comprising reinforcing buffer filaments oriented substantially parallel to each other. According still further to the present invention, the reinforcing buffer filaments are oriented substantially perpendicular to a longitudinal axis of the optical fiber.

The present invention provides a significant improvement over the prior art by the discovery that fiber grating sensors can be embedded within layers of the structure in such a way as to measure when the resin reaches minimum viscosity and when rapid resin crosslinking (or gelation or hardening) occurs, and, more specifically, the discovery that the fiber sensor must be surrounded by minimum thickness buffer regions which allow the grating sensor to exhibit maximum sensitivity to the detection of the minimum resin viscosity and the gelation point (i.e., the onset of a rapid crosslinking rate) of the resin while also isolating the sensor from interfering stresses from arbitrarily angled filaments of regions outside the buffer regions.

Measuring minimum resin viscosity and the gelation point are important because one must know when resin viscosity is lowest in order to apply pressure to force resin uniformly around the reinforcing filaments. Also, one must apply such pressure before such gelation occurs.

Still further, optical fiber grating sensors have a number of features that make them particularly suitable for curing process monitoring of composite materials and structures. For example, they have a small diameter (less than 150 microns outside diameter), they have a small gage length (a quasi-point sensor), they are stable to high temperatures (greater than 400° C.), they adhere well to epoxy resins, they can be multiplexed to provide a large number of sensors along a single fiber while using a single input/output connection, and they are adequately strong and durable (i.e., good strain-to-failure ratio and tensile strength), which provides a fatigue life and testing range greater than required by most composite structure applications. Still further, fiber grating sensors can be conveniently installed in the composite parts as the unconsolidated lay-up is built. In this manner the sensors may be placed at many locations within the structure to perform distributed measurements.

The foregoing and other objects, features and advantages of the present invention will become more apparent in light of the following detailed description of exemplary embodiments thereof as illustrated in the accompanying drawings.

BEST MODE FOR CARRYING OUT THE INVENTION

Figure 1:
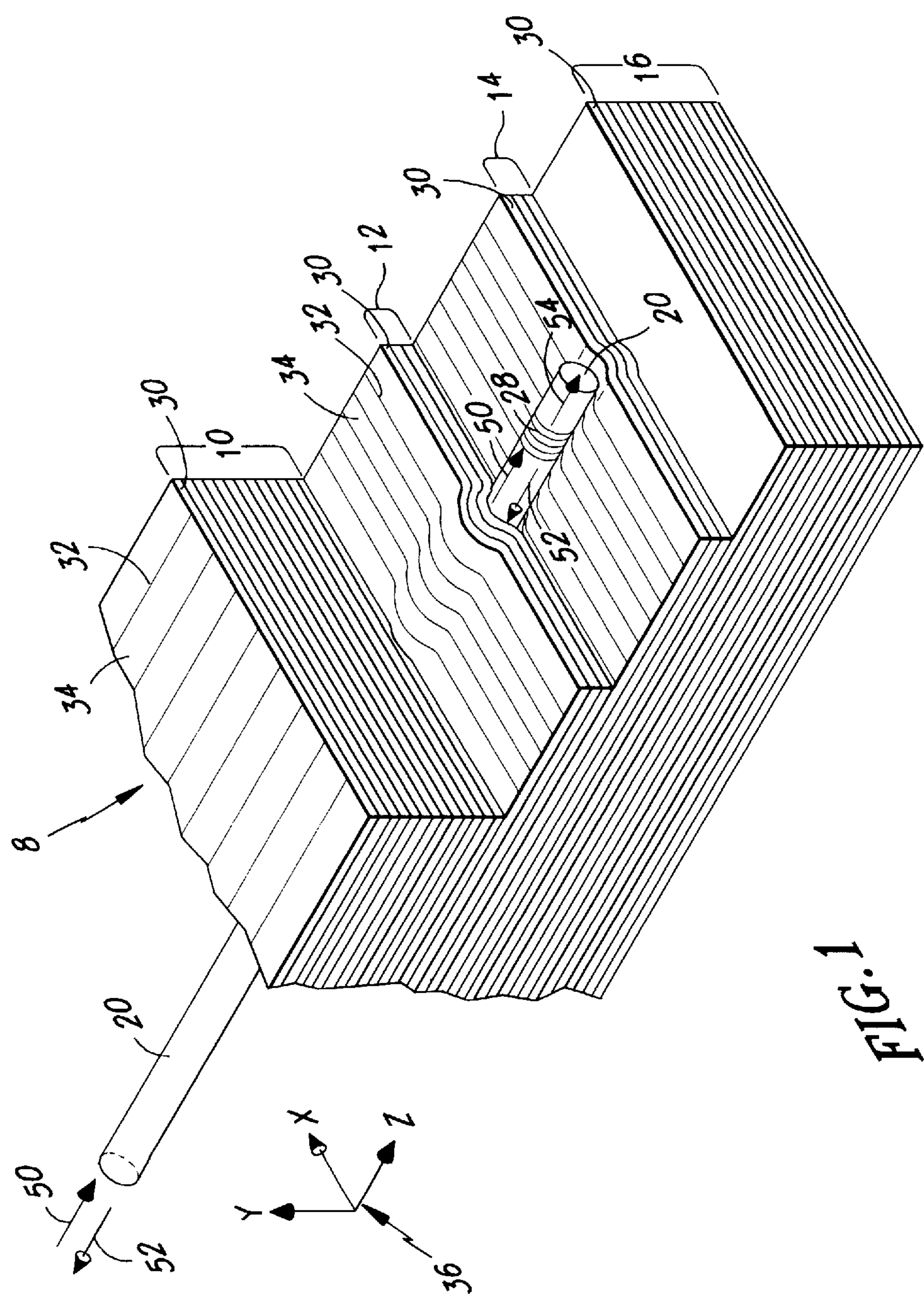
FIG. 1 is a perspective view of a composite structure showing a plurality of layers surrounding a fiber Bragg grating sensor, in accordance with the present invention.

Referring to FIG. 1, an embedded optical fiber sensor for monitoring composite structure resin curing comprises a plurality of regions 10,12,14,16 (discussed hereinafter) and an optical fiber 20 embedded between the regions 12 and 14. The fiber 20 comprises a typical communications single spatial mode fiber having a germania-doped silica core with a diameter of about 6 microns within a silica cladding having a total outer diameter (core and cladding) of about 125 microns. Other fiber compositions, sizes, and modes may be used if desired. Also, fibers with or without outer sheaths or buffer coatings may be used if desired. The core of the fiber 20 has at least one reflective element 28 impressed therein, such as a Bragg grating, similar to that discussed in U.S. Pat. No. 4,806,012, entitled "Distributed, Spatially Resolving Optical Fiber Strain Gauge" and U.S. Pat. No. 4,761,073, entitled "Distributed, Spatially Resolving Optical Fiber Strain Gauge", both to Meltz et al. The grating 28 within the fiber 20 is also called a fiber grating "sensor". The grating sensor 28 has a length (or gage length) of about 1 to 10 mm, making it almost a point-type sensor (i.e., a "quasi-point" sensor). Other lengths may be used if desired.

Each of the regions 10–16 comprise a plurality of layers 30 (for use in a compression molding process). Each of the layers 30 comprise cylindrical reinforcing filaments 32 made of graphite which are embedded in the layers 30 in predetermined directions. The filaments 32 within a given one of the layers 30 are substantially parallel to each other. Between and around the filaments 32 is a known polymer matrix 34, e.g., a thermal set epoxy resin, known in the industry. Other materials may be used for the filaments 32, and other thermal set polymer matrix materials may be used for the regions 34 therebetween, if desired. For example, the filaments 32 may be made of glass, nylon, cloth, KEVLAR® (polymer filament), or other materials. Also, one or more of the layers 30 may instead be made of fiberglass reinforced polymer resin or other materials. Also, the filaments 32 need not be cylindrical in shape. The layers 30 are also called "plies" and the total laminated structure 8 is referred to as a "lay-up" (or laminate or composite structure).

For the lay-up of FIG. 1, the regions 12,14, which are immediately adjacent to and surround the optical fiber 20, each have three of the layers 30 all having the filaments 32 oriented along the x-axis of an "xyz" coordinate axis system 36, which is 90° from (or perpendicular to) the longitudinal axis (or z-axis) of the optical fiber 20 along which light propagates. The regions 12,14 are referred to as "buffer" regions, as discussed hereinafter. The other regions 10,16 that surround the buffer regions 12,14 have filaments 32 oriented at arbitrary angles relative to the fiber 20. Accordingly, the lay-up 8 of FIG. 1 has a pattern: [arbitrary, 90°,90°,90°] fiber [90°,90°,90°, arbitrary].

The lay-up of FIG. 1 having any variation of filament orientation can be manufactured by a variety of methods, as discussed hereinbefore in the Background Art section hereto. For example, the layers 30 may be prefabricated, having the filaments 32 pre-impregnated with the resin 34 therebetween. The layers 30 may then be assembled in the desired lay-up pattern with the fiber 20 located between the desired layers at the desired location. The assembly is then consolidated in a closed mold or hot press process. Alternatively, a dry cloth lay-up may be assembled in a similar fashion for use in a closed, resin injection molding process, as discussed hereinbefore. For either process, the resin is raised to a temperature at which a chemical reaction occurs to cause polymerization (i.e., curing) of the matrix, which then hardens and is cooled (discussed more hereinafter). Other manufacturing techniques may be used if desired.

Figure 2:
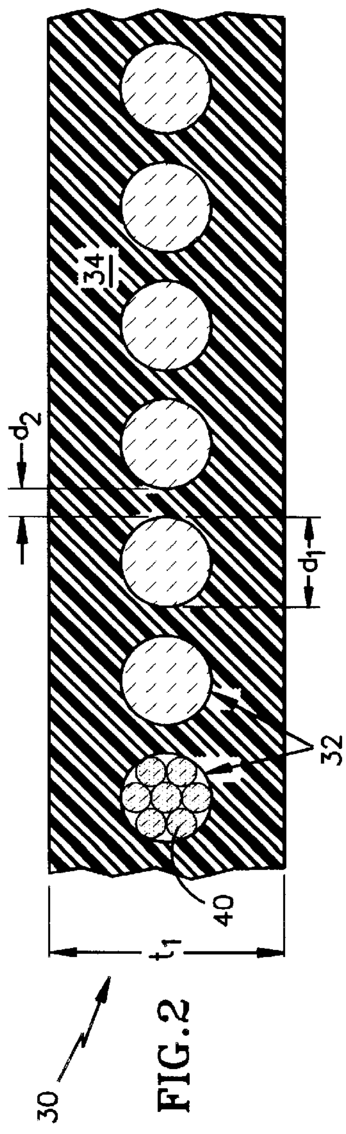
FIG. 2 is a side view of a single layer of the composite structure of FIG. 1 showing reinforcing filaments in accordance with the present invention.

Referring to FIG. 2, each of the filaments 32 may actually be a twisted bundle of graphite fibers (or strands) 40 much finer than the filaments 32. The filaments 32 are surrounded by the resin 34 and have a typical diameter $d_1$ of about 5–10 microns and are separated from each other in a given layer by a distance $d_2$ determined by the desired percentage volume of reinforcing graphite (e.g., 50–70%) of the total volume of a given layer. The thickness $t_1$ of each layer is about 10 mils (0.010") before curing, and approximately 5 mils (0.005") after curing. Other thicknesses, diameters, and percent volumes may be used if desired. Also, the filaments 32 need not be a twisted bundle, but may be solid.

It should be understood that the layers 30 of FIGS. 1 and 2 are idealized isolated layers 30 and that, in the final laminated composite structure after consolidation, the layers 30 are not as well defined. In particular, filaments from one layer may likely be shifted during the curing process and become relocated between the filaments of other layers, and the resin 34 between and around the filaments of one layer will combine with resin from other layers, thereby removing any distinct boundary between layers.

Referring to FIG. 1, as is known, when the fiber 20 with the Bragg grating 28 is embedded in a structure and used as a sensor, a light 50 is injected into one end of the fiber 20, as discussed in the aforementioned U.S. patents to Meltz et al. The grating 28 reflects a predetermined narrow wavelength band of the light 50 as return (or reflected) light 52, thereby allowing the remaining wavelengths of the light 50 to pass through the grating 28 as the light 54. The return light 52 (and/or the passed light 54) is analyzed, e.g., by a spectrum analyzer (not shown), to determine the shift in grating reflection wavelength $\lambda_B$ caused by changes in strain and/or temperature of the structure 8 that the sensor 28 is embedded within.

We have found that when the optical fiber 20 with the grating sensor 28 is surrounded by the immediately neighboring (upper and lower) buffer regions 12,14 having the reinforcing filaments 32 oriented at an angle of 90° with respect to the z-axis of the fiber 20, the sensor 28 exhibits maximum sensitivity to changes in resin parameters through different stages of the resin curing process (discussed hereinafter). The filaments 32 of the layers 30 in the outer regions 10,16 may be oriented in any direction desired for the structure. Other orientations of the filaments 32 in the buffer regions 12,14 will work, but the response of the sensor 28 will not be optimized (as discussed hereinafter).

Figure 3:
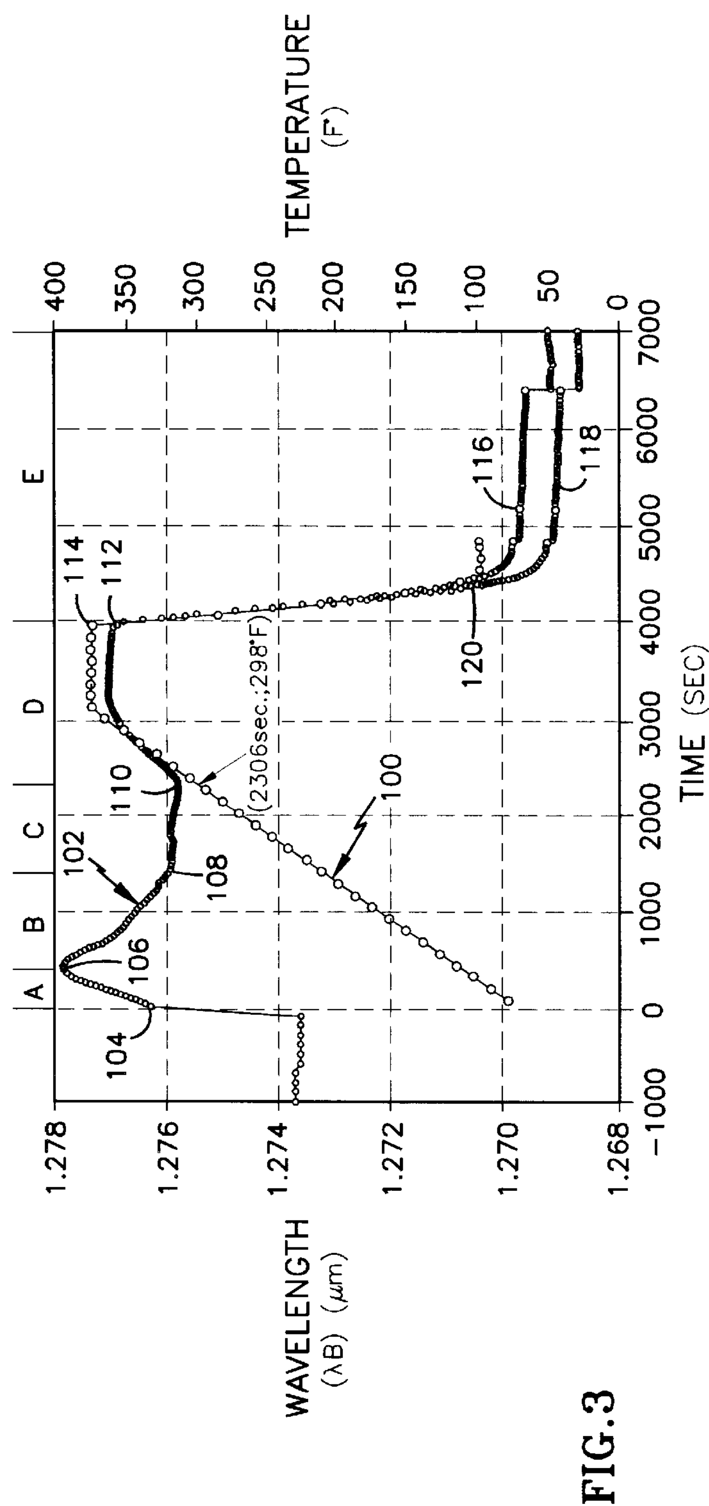
FIG. 3 is a graph of temperature and sensor reflection wavelength versus time for a Bragg grating sensor oriented 90° from the direction of adjacent reinforcing filaments, in accordance with the present invention.

Referring now to FIG. 3, a graph of temperature versus time is indicated by a curve 100 and superimposed thereon is a graph of central reflection (or reflectivity) wavelength $\lambda_B$ of the Bragg grating sensor 28 versus time as indicated by a curve 102. The curves 100,102 are plotted during a composite lamination process of the lay-up 8 of FIG. 1 having three uni-directional layers in each of the buffer regions 12,14 with all the filaments 32 being oriented along the z-axis (perpendicular to the optical fiber 20), and the other regions 10,16 are non-existent. After the preformed lay-up is placed in a molding hot press tool, some pressure is applied to stabilize the arrangement and to keep its alignment from shifting. This application of transverse pressure creates microbending changes in the filter function of the sensor 28 (FIG. 1), thereby increasing its reflection wavelength, as indicated by a wavelength point 104. The forces exerted by the filaments 32 on the surface of the sensor 28 increase as the temperature 100 increases, as indicated by the positive slope of the curve 102 during a region A of the curing process. The transverse stress disturbance on the sensor 28 continues to increase until a point 106 at a well-identifiable temperature (e.g., 110° F.) where the viscosity of the resin begins to drop and the resin becomes softer and more fluid-like. As this change occurs, the resin can no longer force the reinforcing filaments to apply transverse pressure disturbances on the optical fiber sensor 28. As a result, the transverse stress on the fiber sensor 28 begins decreasing and the associated wavelength shift does also, as indicated by a negative slope of the curve 102 over a region B of the profile 102. As the resin reaches its most fluid-like condition, during a region C, much of the transverse stress disappears because the reinforcing filaments are now free to reposition themselves within the hydrostatic environment of the low viscosity resin. In many manufacturing processes, this is the best time to apply increased pressure on the lay-up by increasing the force on the molding tool in the hot press, which will further insure uniform flow of resin throughout the structure.

As the temperature of the curing process continues to increase throughout the region C, the resin begins to crosslink (or harden). At a point 110 (also known as the "gelation" point), the rate of crosslinking greatly increases and the resin begins to adhere to the surface of the optical fiber sensor 28. Subsequently, as the temperature of the curing process increases further, the resin expands because it has a positive thermal expansion coefficient. As a result, because the resin is now hardening around the sensor and is adhering thereto, as the material expands, it imposes a strain on the sensor 28, as indicated by a region D. The positive-sloped portion of the curve 102 (beginning at the point 110) of the region D, is indicative of an increasing strain on the sensor while the temperature continues to rise. The onset of this increasing strain provides a strong indication of the gelation point.

During most manufacturing processes it is useful to have the gelation point occur uniformly throughout the structure to optimize structural integrity. Thus, the optical fiber sensor 28 can be used to diagnose this effect when it is placed in a structure as indicated herein.

Finally, after the part reaches the full curing temperature and time at a point 114 on the temperature curve 100, it is cooled over a cooling region E. Since the sensor 28 was "frozen" within the resin (i.e., the resin hardened and bonded to the sensor) when the resin was in an expanded state at elevated temperature, the sensor 28 measures compressive strain as the structure cools down. This is indicated by a negative slope of the profile 102 beginning at a point 114 and continuing while the temperature drops over the region E. Due to the non-uniform, transverse compressive stresses on the fiber sensor 28 after cooling, the reflected wavelength curve 102 splits into two curves 116,118 at a point 120 which indicates induced birefringence in the fiber 20. At the end of the cooling cycle E, the sensor 28 provides a measurement dominated by the final residual shrinkage of the part along the z-axis direction.

Thus, the sensor 28 also provides a quantitative assessment of the residual strain on and shrinkage of the structure as it cools. Such shrinkage measurement can help guide the development of a curing process that minimizes warpage so as to limit the amount of post-cure machining required to achieve the final specified dimensions of the desired structure.

Thus, three key aspects of composite structure resin cure are shown by the sensor 28 surrounded by the buffer regions 12,14 of the present invention: (1) the minimum viscosity of the resin, (2) the gelation point (i.e., the onset of a rapid crosslinking rate) of the resin, and (3) the residual strain in the structure. Each of these curing phases are easily identified in the sensor data shown in FIG. 3 for the fiber grating sensor 28 placed at 90° to the reinforcing filaments 32 of the buffer regions 12,14.

Figure 4:
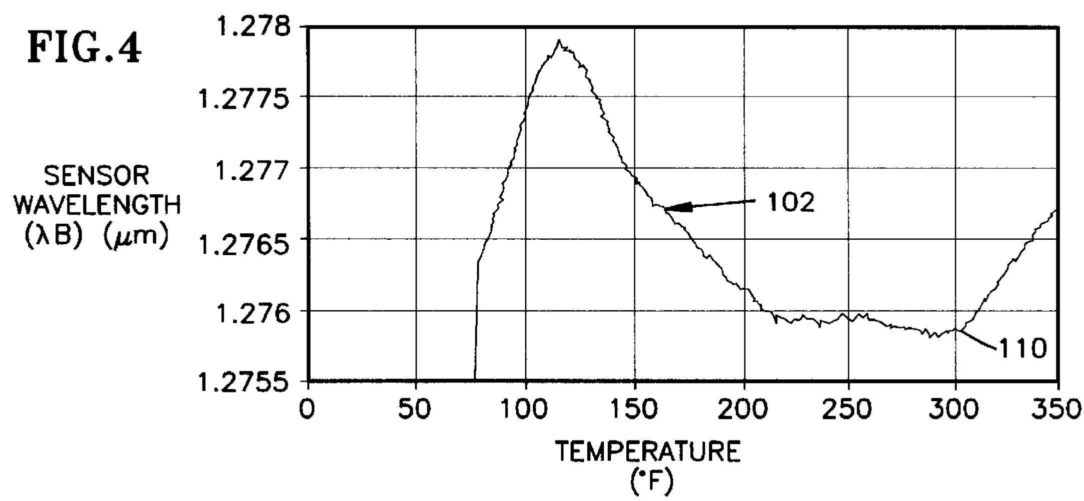
FIG. 4 is a blow-up of the graph of reflection wavelength versus temperature of the sensor of FIG. 3, in accordance with the present invention.
Figure 5:
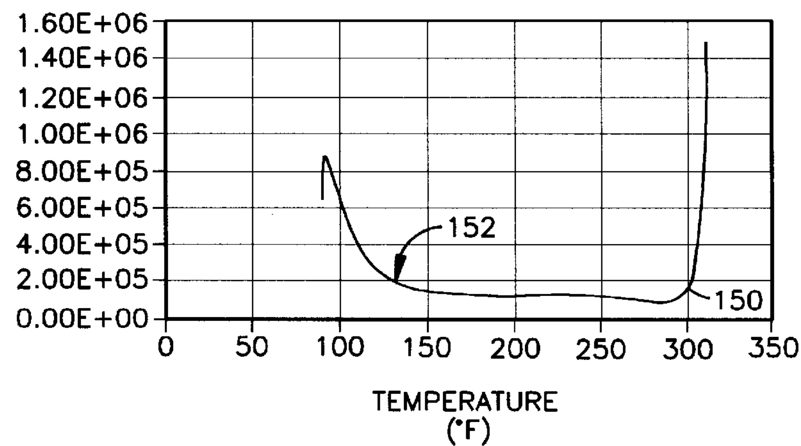
FIG. 5 is a graph of rheologic viscosity versus temperature which verifies the results of FIG. 3, in accordance with the present invention.
Figure 6:
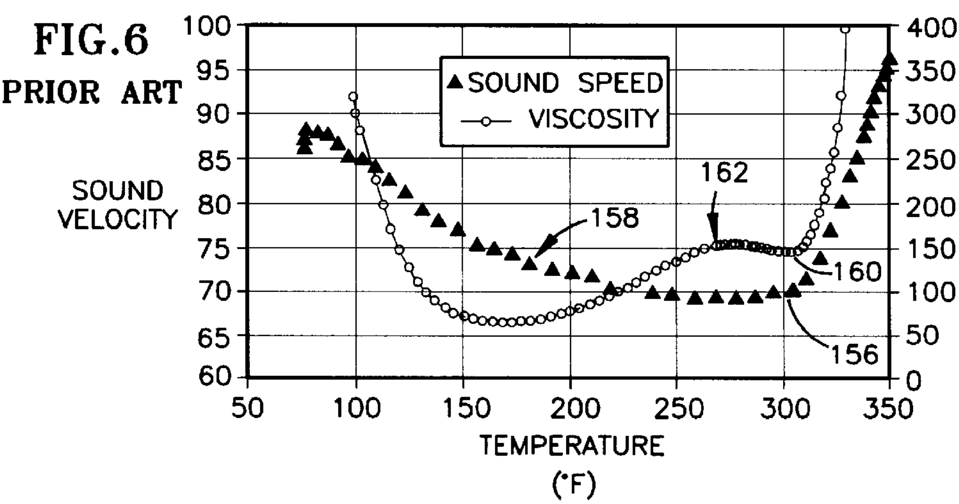
FIG. 6 is a graph of sound velocity versus temperature which verifies the results of FIG. 3, in accordance with the present invention.

Referring now to FIGS. 4,5, and 6, the results of FIG. 3 are verified using two comparison techniques run over the same temperature profile 100 shown in FIG. 3. First, referring to FIG. 4, a blowup of the regions A,B,C, and a portion of D of FIG. 3 shows the point 110 where gelation occurs and is shown for comparison with FIGS. 5 and 6.

Referring to FIG. 5, using a rheologic viscosity test which is done off-line, as is known (discussed hereinbefore in the Background Art section), the point at which the viscosity increases greatly is indicated at a point 150 on a viscosity curve 152 which matches with the point 110 of FIGS. 3 and 4. Also, referring to FIG. 6, using a sound velocity technique known in the art (discussed hereinbefore in the Background Art section), the gelation point occurs at a point 156 on a sound velocity curve 158 (and at a point 160 of a related viscosity curve) which agrees with the point 110 of FIGS. 3 and 4. However, use of the fiber grating sensor 28 can provide more accurate information than that of the off-line rheologic method and can provide distributed measurements not available by the sound velocity method. In particular, as discussed hereinbefore, the rheologic viscosity test is done off-line on a material sample from the structure, not during the curing process itself. Further, as also discussed hereinbefore, while the sound velocity technique is performed during the curing process, it requires ultrasonic transducers for propagating sound waves transverse through the lay-up and ultrasonic sensors for sensing the sound velocity at the opposite side. Also, such a technique provides only an average viscosity measurement across the structure with no through-the-thickness distributed measurements. For the tests performed in FIGS. 4,5, and 6, the lay-up was the same lay-up as that described for FIG. 3 (i.e., three of the layers 30 in each of the buffer regions 12,14 and no layers in the other regions 10,16), and thus, the lay-up was quite thin. Accordingly, the average viscosity indications would be substantially the same as that at the middle of the part and, thus, can be used to compare with the fiber grating sensor technique.

Figure 7:
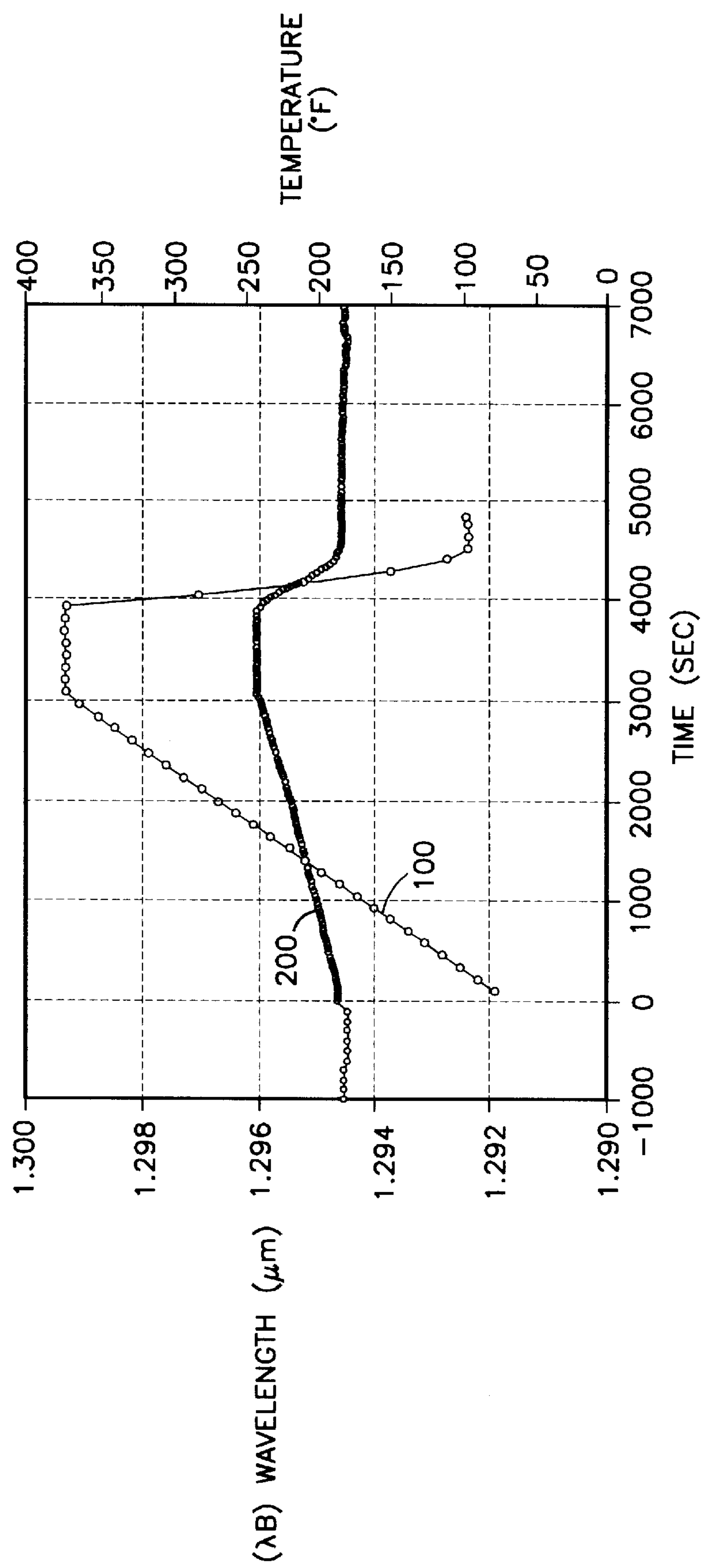
FIG. 7 is a graph of wavelength and temperature versus time for a Bragg grating sensor oriented in the same direction as adjacent reinforcing filaments, in accordance with the present invention.

Referring now to FIG. 7, the temperature profile 100 is plotted against the reflection wavelength of the grating sensor 28 (similar to FIG. 3), as indicated by a curve 200 both plotted against time, with the filaments 32 of the buffer regions 12,14 oriented along the z-axis of the fiber, i.e., 0° from the z-axis of the fiber. The lay-up used is the same lay-up as that described for FIG. 3 (i.e., three of the layers 30 in each of the buffer regions 12,14 and no layers in the other regions 10,16). As can be seen, the results do not as clearly show the minimum viscosity and gelation effects which were shown in FIG. 3 when the fiber was perpendicular to the filaments in the layers 12,14.

Accordingly, we have found that maximum sensor sensitivity occurs with the filaments 32 in the buffer regions 12,14 oriented perpendicular to the longitudinal axis of the optical fiber 20 because the filaments 32 do not constrain the longitudinal response of the sensor 28 and the thermal expansion coefficient of the resin 34 is much greater than that of the filaments 32. Consequently, when the filaments 32 in the buffer regions 12,14 are oriented perpendicular to the optical fiber 20, as in FIG. 3, strain along the longitudinal axis of the optical fiber 20 will be dominated by the thermal expansion coefficient of the resin 34 (once gelation has occurred). Conversely, if the filaments 32 in the buffer regions 12,14 are parallel with the optical fiber 20, as in FIG. 8, the sensor 28 is constrained by the high stiffness of the filaments (the stiffness of the filaments 32 being much greater than the stiffness of the resin) as well as the smaller expansion coefficient of the filaments 32, making it difficult for the sensor to detect changes in the state of the resin. Further, orientations of the filaments 32 in the buffer regions 12,14 other than 90 degrees will work, but the response of the sensor 28 will not be optimized. Also, as discussed hereinbefore, the filaments 32 of the layers 30 in the outer regions 10,16 may be oriented in any direction desired for the structure.

Figure 8:
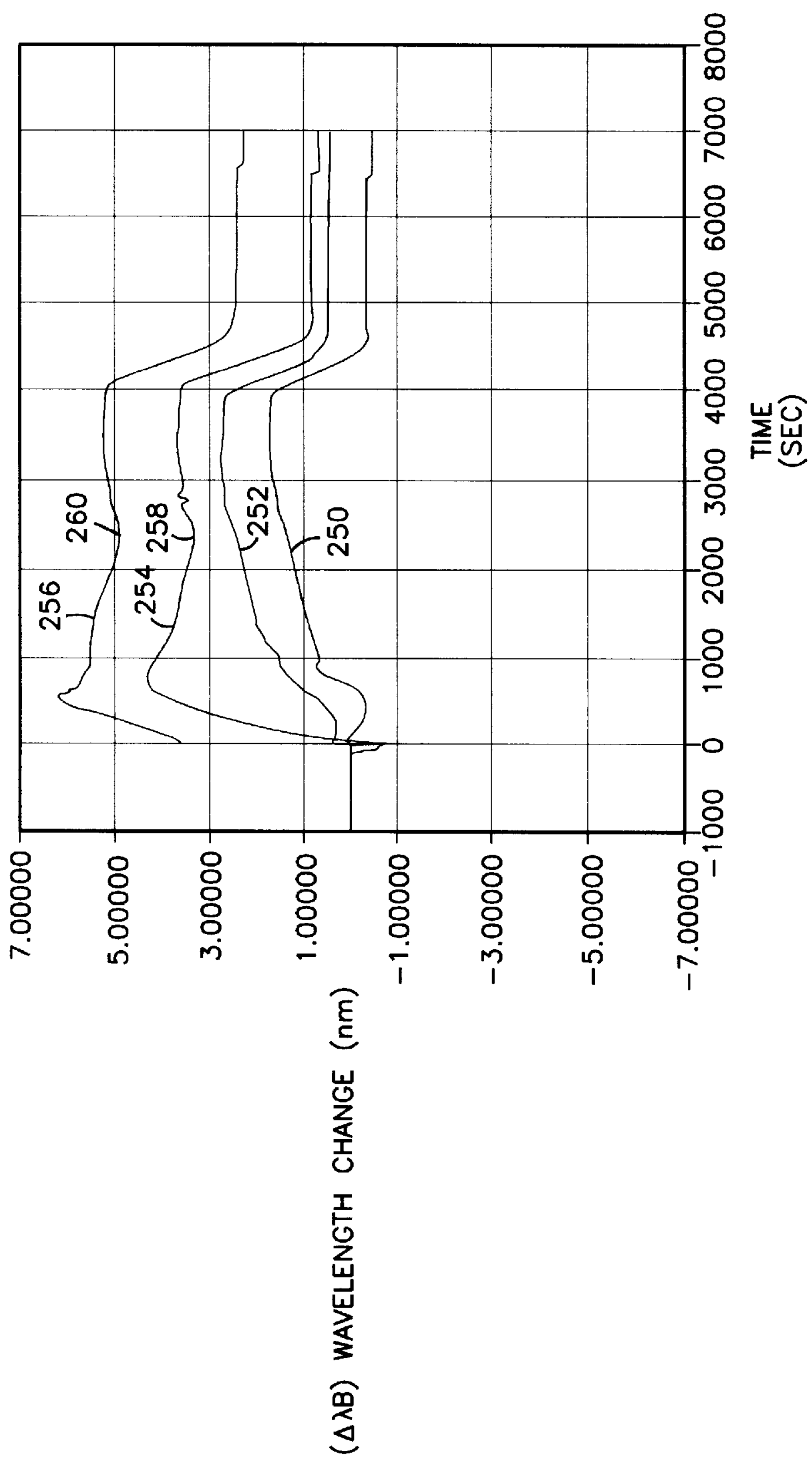
FIG. 8 is a family of curves of sensor reflection wavelength change vs. time for various thicknesses of buffer regions surrounding the sensor, in accordance with the present invention.

Referring now to FIGS. 1 and 8, we have also found that at least three of the layers 30 (at the precured thickness $t_1$ discussed hereinbefore) are required in each of the buffer regions 12,14 surrounding the fiber grating sensor 28 to provide detection of the minimum resin viscosity and gelation of the resin 34 when embedded in a larger lay-up (i.e., when the outer regions 10,16 have at least one layer in them). In particular, the buffer regions 12,14 protect or isolate the fiber 20 and the sensor 28 from interfering stresses from the arbitrarily angled filaments 32 of the layers (or plies) 30 of the outer regions 10,16.

Referring to FIG. 8, more specifically, four curves 250, 252,254,256 represent the sensor reflection wavelength change ($\Delta\lambda_B$) from an initial sensor reading (before heating occurs) over the temperature profile 100 of FIG. 3 (not shown in FIG. 8) for a configuration where each of the buffer regions 12,14 has one layer, two layers, three layers, and four layers, respectively. Also, the lay-up used to generate the results of FIG. 8 has a single layer 30 (or face ply) in the outer regions 10 and 16 (FIG. 1) having filaments 32 oriented along the z-axis of the fiber 20 to hold the structure together and exert cross-ply interfering stresses on the sensor 28. When each of the buffer regions 12,14 have one or two layers 30 therein, the curves 250,252 do not provide an accurate indication of when minimum resin viscosity and gelation point occurs. However, when three layers are used in each of the buffer regions 12,14, the curve 254 shows that the gelation point occurs at a point 258, similar to that shown in FIG. 3. Similarly, when four layers 30 are used in each of the buffer regions 12,14, the curve 256 shows that the gelation point occurs at a point 260. Thus, to adequately detect minimum resin viscosity and gelation the minimum number of layers required for the buffer regions 12,14 around the fiber 20 is three. Although more layers may be used for the buffer regions 12,14, it is typically desirable to minimize the number of layers which have filaments oriented in the same direction (i.e., uni-directional plies). Accordingly, the sensor 28 must have at least three uni-directional layers or plies (each ply having the thickness $t_1$ discussed hereinbefore) on each side of the sensor 28 to maintain an accurate sensor response to resin viscosity changes. If the layers 30 are thicker or thinner than those discussed herein, the number of layers 30 needed in the buffer regions 12,14 is less or more, respectively, provided the resulting buffer regions 12,14 isolate the fiber from stresses from the layers of the outer regions 10,16.

while the invention has been shown as having the filaments 32 of the buffer regions 12,14 as being perpendicular to the longitudinal or z-axis of the fiber 20, it should be understood that this orientation provides maximum sensitivity to changes in resin parameters, in particular, the detection of minimum resin viscosity and the gelation point (i.e., the onset of a rapid crosslinking rate) of the resin. As the angle of the filaments deviates from 90°, the sensitivity to such resin changes is reduced thus the corresponding changes in $\lambda_B$ are much smaller in magnitude, making detection by the grating sensor 28 more difficult or impossible to observe depending on the presence of other noise sources and the sensitivity of the external optical detection equipment (e.g., a spectrum analyzer).

Further, is should be understood that the filaments and/or resin in the buffer regions 12,14 need not be made of precisely the same material as the filaments and/or resin of the outer regions 10,16 of the structure, provided the buffer regions 12,14 exhibit characteristics which are representative of the resin curing characteristics of the outer regions 10,16. For example, the filaments 32 in the buffer regions 12,14 may be made of glass, while the filaments 32 in the outer regions 10,16 may be made of graphite, or visa versa. Still further, instead of the buffer regions 12,14 having filaments and/or resin therein, any other buffer means which is adjacent to the sensor and allows the sensor to detect a minimum resin viscosity and a gelation point of the resin and which isolates the sensor from interfering stresses from other portions of the composite structure (i.e., the outer regions 10,16) may be used if desired.

Also, more than one sensor 28 may be embedded along the fiber 20 to detect resin changes at distributed points along the structure. In that case, sensor multiplexing techniques may be used such as those described in U.S. Pat. Nos. 4,996,419 entitled "Distributed Multiplexed Optical Fiber Bragg Grating Sensor Arrangement" to Morey; 5,401,956 entitled "Diagnostic System for Fiber Grating Sensors", to Dunphy et al.; and 5,426,297 entitled "Multiplexed Bragg Grating Sensors", to Dunphy et al. Additionally, a plurality of optical fibers or one long optical fiber may be distributed along the x-axis of the structure 8 (along a layer). Further, a plurality of optical fibers together with the accompanying buffer layers 12,14, may be distributed along the y-axis (or thickness) of the structure 8. A structure may contain many hundreds of the layers 30, having a plurality of the optical fibers 20 and sensors 28 (together with the buffer layers 12,14) distributed at strategic measurement points throughout the thickness of the structure. Accordingly, the invention provides insight into when various regions of the structure have reached minimum resin viscosity and then reached the gelation point, thereby allowing for the optimal curing process to be designed for a given structure.

For example, having a plurality of sensors throughout the thickness of the structure 8 allows an optimal temperature curing profile to be designed such that curing will occur for the outer surfaces at a more appropriate time relative to when it occurs for the middle regions, thereby minimizing trapped gases within the lay-up.

The invention may be used in a production process in numerous different ways. For example, the invention may be used to design an optimal curing process to configure an initial setup which then is used for all subsequent processing of similar structures. Alternatively, each lot of preimpregnated material received may be fitted with such a sensor so as to lot-test each batch of material for optimal curing. Alternatively, every structure created may be fitted with such sensors, if desired.

Once the laminated structure is fabricated, the regions of the structure having the optical fibers 20 and sensors 28 may be cleaved off or, alternatively, the optical fibers 20 and sensors 28 may remain inside the structure to provide strain measurements of the completed structure while the structure is in use.

If it is desired to leave the optical fibers 20 and sensors 28 within the structure we have found that in order for the fiber 20 and sensor 28 to not adversely affect the strength of the resultant material, they must: (1) have a small overall diameter, e.g., less than 150 microns (including core, cladding, and sheath); (2) have a high tensile strength, e.g., greater than 100K lbs per square inch (psi) and large strain-to-failure ratio, e.g., greater than 1% (length extension before breaking); and (3) bond well to the composite structure (resin and filaments). Certain standard communications fibers have these characteristics, as discussed hereinbefore.

Although the invention has been described and illustrated with respect to the exemplary embodiments thereof, it should be understood by those skilled in the art that the foregoing and various other changes, omissions and additions may be made without departing from the spirit and scope of the invention.

I claim:

1. A composite structure resin cure monitoring apparatus, comprising:

an optical fiber having a grating sensor embedded therein;

buffer means disposed adjacent to said sensor;

a composite structure disposed adjacent to said buffer means; and said buffer means for enabling said sensor to detect a minimum resin viscosity and a gelation point of the resin and for isolating said sensor from interfering stresses from said composite structure.

2. The cure monitoring apparatus of claim 1 wherein said composite structure comprises a predetermined number of outer layers each of said outer layers having reinforcing outer filaments, each of said outer filaments in a given one of said outer layers being oriented substantially parallel to each other, and the orientation of said outer filaments in each of said outer layers being arbitrary relative to the orientation of said buffer filaments.

3. The cure monitoring apparatus of claim 1 wherein said buffer means comprises a predetermined number of layers each of said layers comprising reinforcing buffer filaments oriented substantially parallel to each other.

4. The cure monitoring apparatus of claim 3 wherein said reinforcing buffer filaments are oriented substantially perpendicular to a longitudinal axis of said optical fiber.

5. The cure monitoring apparatus of claim 4 wherein each of said layers in said buffer means has a pre-cured thickness of about 10 mils (0.010") and wherein said pre determined number of said layers is at least three.

6. A method for making a composite structure resin cure monitoring apparatus, comprising the steps of:

obtaining an optical fiber having a grating sensor embedded therein;

surrounding said sensor with buffer regions:

surrounding said buffer regions with a composite structure; and said buffer regions enabling said sensor to detect a minimum resin viscosity and a gelation point of the resin and isolating said sensor from interfering stresses from said composite structure.

7. The method of claim 6 wherein said composite structure comprises a predetermined number of outer layers each of said outer layers having reinforcing outer filaments, each of said outer filaments in a given one of said outer layers being oriented substantially parallel to each other, and the orientation of said outer filaments in each of said outer layers being arbitrary relative to the orientation of said buffer filaments.

8. The method of claim 6 wherein said buffer regions comprise a predetermined number of layers each of said layers comprising reinforcing buffer filaments oriented substantially parallel to each other.

9. The method of claim 8 wherein said reinforcing buffer filaments are oriented substantially perpendicular to a longitudinal axis of said optical fiber.

10. The method of claim 9 wherein each of said layers in said buffer means has a pre-cured thickness of about 10 mils (0.010") and wherein said predetermined number of said layers is at least three.

* * * * *